United States Patent
Min

(10) Patent No.: US 6,180,599 B1
(45) Date of Patent: Jan. 30, 2001

(54) PHARMACEUTICAL COMPOSITION, CONTAINING MEDIUM-CHAIN FATTY ACIDS AS ACTIVE INGREDIENTS, FOR DENTAL CARIES AND PERIODONTAL DISEASE

(76) Inventor: Byung-Moo Min, #13-501 Rex Apt., 300-3 Ichon-dong, Yongsan-ku, Seoul 140-030 (KR)

(*) Notice: Under 35 U.S.C. 154(b), the term of this patent shall be extended for 0 days.

(21) Appl. No.: 09/381,933

(22) PCT Filed: Mar. 26, 1998

(86) PCT No.: PCT/KR98/00063

§ 371 Date: Sep. 27, 1999

§ 102(e) Date: Sep. 27, 1999

(87) PCT Pub. No.: WO98/43601

PCT Pub. Date: Oct. 8, 1998

(30) Foreign Application Priority Data

Mar. 28, 1997 (KR) .................................. 97/11244

(51) Int. Cl.[7] .................. A61K 31/185; A61K 38/00; A61K 7/18
(52) U.S. Cl. .................... 514/8; 514/558; 424/52
(58) Field of Search .................... 514/2, 578; 424/49, 424/52, 58

(56) References Cited

U.S. PATENT DOCUMENTS

| | | | |
|---|---|---|---|
| 3,952,092 | * 4/1976 | Bowen et al. | 424/50 |
| 4,217,341 | * 8/1980 | Suddick et al. | 424/48 |
| 4,353,892 | * 10/1982 | Caslavsky et al. | 424/52 |
| 4,533,544 | * 8/1985 | Groat et al. | 424/52 |
| 4,540,576 | * 9/1985 | Zahradnik | 424/676 |
| 4,619,825 | * 10/1986 | Eigen et al. | 424/49 |
| 4,737,359 | * 4/1988 | Eigen et al. | 424/50 |
| 4,942,034 | * 7/1990 | Hill et al. | 424/401 |
| 4,976,954 | * 12/1990 | Kleber et al. | 424/52 |
| 4,988,499 | * 1/1991 | Bristow et al. | 424/52 |
| 5,098,711 | * 3/1992 | Hill et al. | 424/401 |
| 5,240,710 | * 8/1993 | Bar-Shalom et al. | 424/422 |
| 5,284,648 | * 2/1994 | White et al. | 424/49 |
| 5,416,075 | * 5/1995 | Carson et al. | 514/23 |
| 5,679,377 | * 10/1997 | Bernstein et al. | 424/491 |
| 5,824,292 | * 10/1998 | Carr et al. | 424/49 |
| 5,840,338 | * 11/1998 | Roos et al. | 424/488 |
| 5,962,428 | * 10/1999 | Carrano et al. | 514/44 |

FOREIGN PATENT DOCUMENTS

0481701 * 4/1992 (EP) .

OTHER PUBLICATIONS

Hayers et al., The effects of medium chain fatty acids and fluoride on . . . , Arch. Oral Biol., vol. 35/12, pp. 939–943, (1990).*

Copy of chemical seach abstract from Registry.*

* cited by examiner

Primary Examiner—William R. A. Jarvis
Assistant Examiner—Vickie Kim
(74) Attorney, Agent, or Firm—Bachman & LaPointe, P.C.

(57) ABSTRACT

The present invention relates to a new use of medium-chain fatty acids in prevention and treatment of dental caries and a pharmaceutical composition containing medium-chain fatty acids as active ingredients.

Particularly, the present invention relates to the use of the salt form of medium-chain fatty acids; nonanoic acid, capric acid, undecanoic acid, lauric acid, tridecanoic acid or myristic acid, for prevention and treatment of dental caries and periodontal disease. The pharmaceutical composition containing medium-chain fatty acids as active ingredients may include lectins and/or fluoride in addition to medium-chain fatty acids.

7 Claims, 16 Drawing Sheets

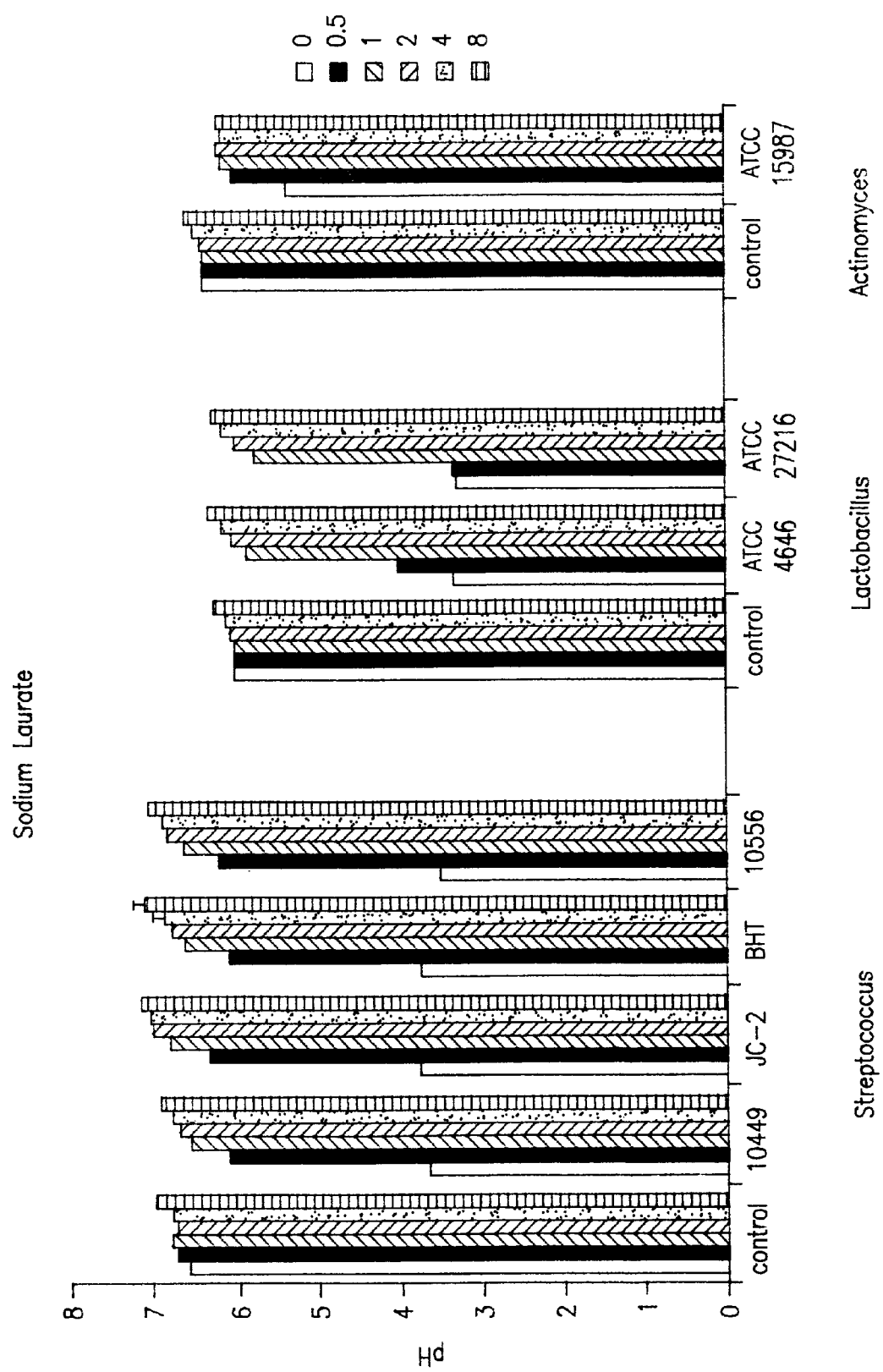
FIG. IE

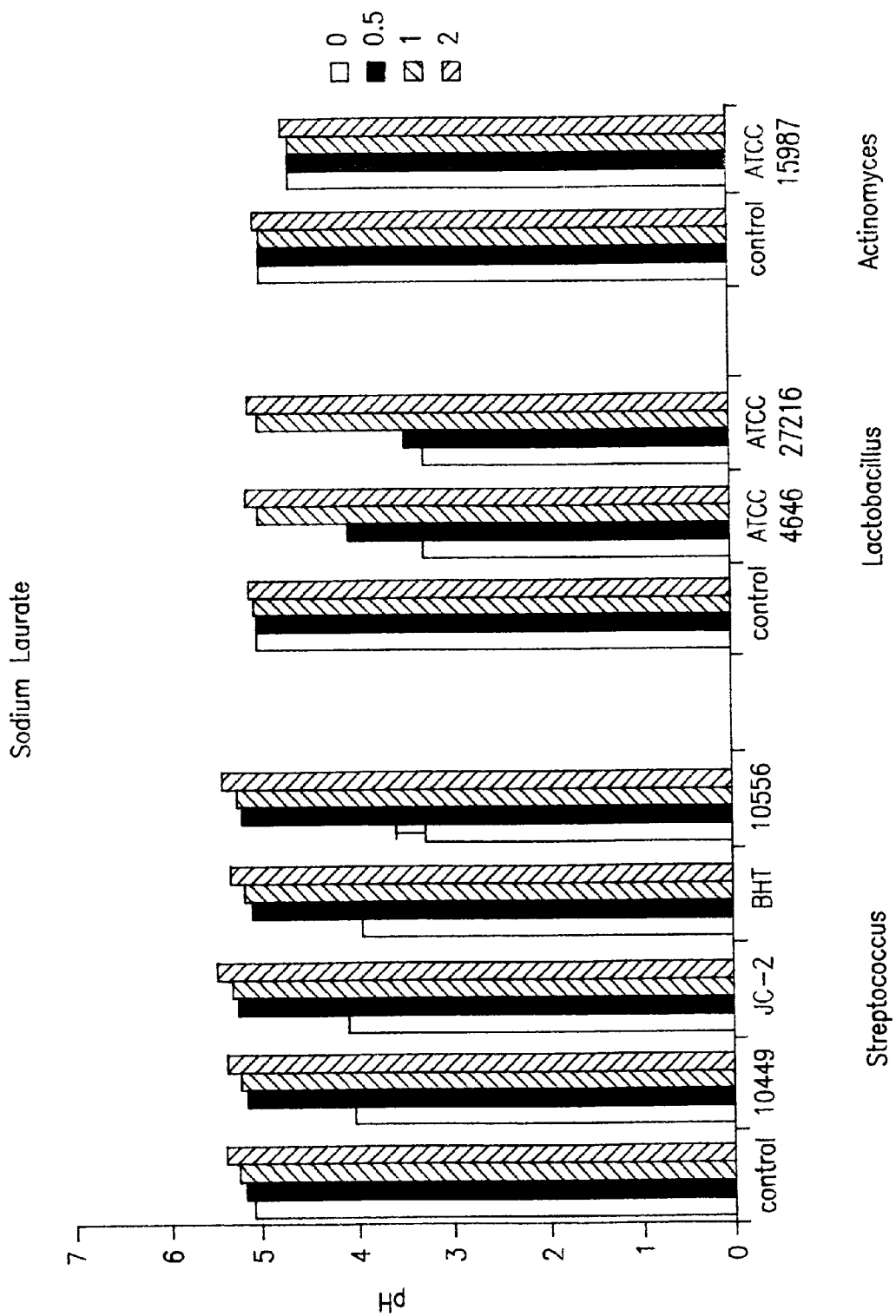
FIG. IF

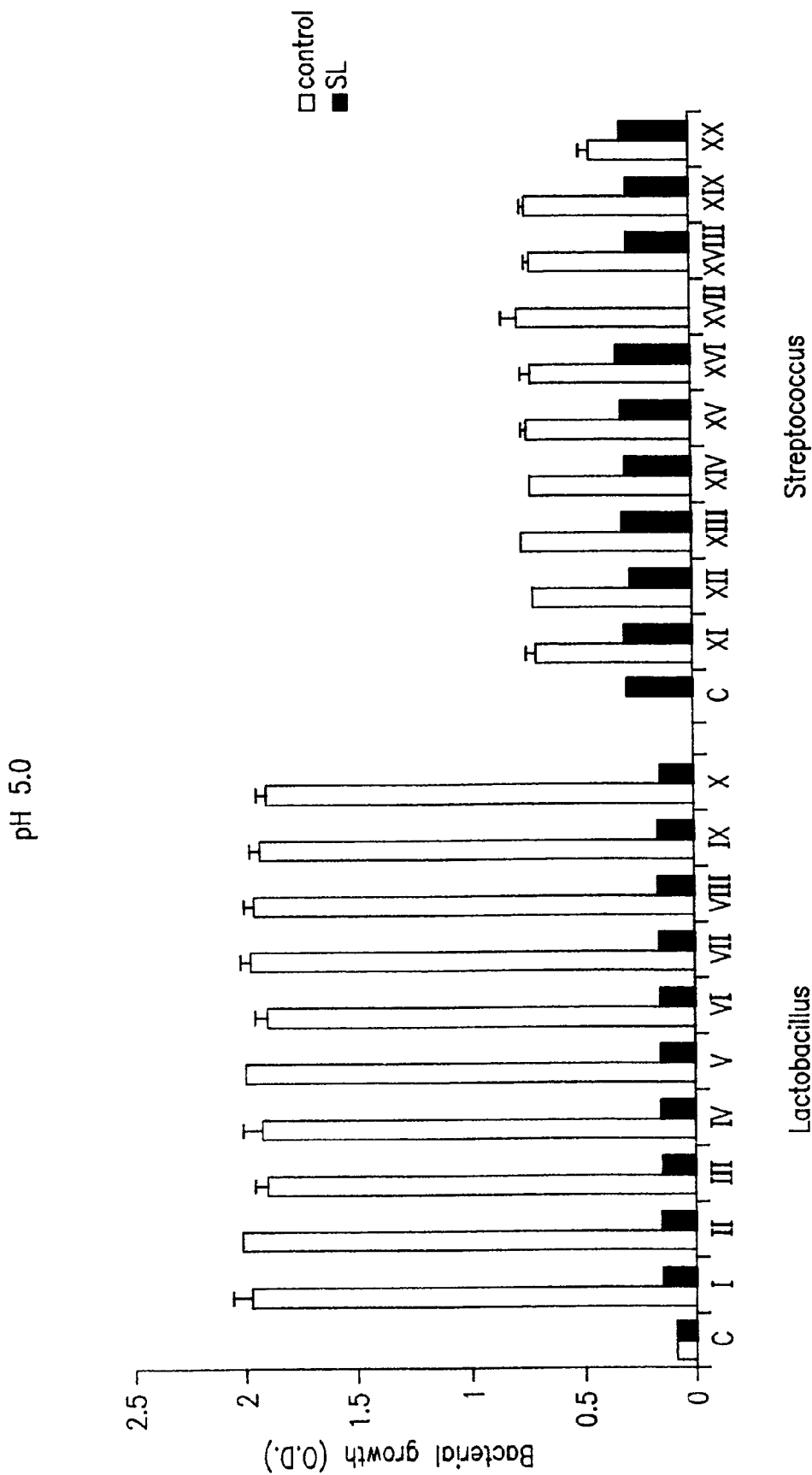

PHARMACEUTICAL COMPOSITION, CONTAINING MEDIUM-CHAIN FATTY ACIDS AS ACTIVE INGREDIENTS, FOR DENTAL CARIES AND PERIODONTAL DISEASE

BACKGROUND OF THE INVENTION

The present invention relates to a new use of medium-chain fatty acids as a prophylactic against dental caries and as a therapeutic treatment of the disease, and a pharmaceutical composition containing these medium-chain fatty acids as active ingredients.

Particularly, the present invention relates to the use of the salt form of specific medium-chain ($C_9$–$C_{14}$) fatty acids; nonanoic acid ($C_9$) capric acid ($C_{10}$), undecanoic acid ($C_{11}$), lauric acid ($C_{12}$), tridecanoic acid ($C_{13}$) or myristic acids ($C_{14}$), as a prophylactic against dental caries and therapeutic treatment of the same disease and periodontal disease. The pharmaceutical composition of these medium-chain fatty acids may include lectins and/or fluoride as well.

Dental caries, one of the most prevalent and significant forms of oral disease, can lead to loss of teeth in spite of development of therapeutics. Caused by dental plaque formed on the surface of teeth, dental caries results in tooth loss as a result of organic acids, the natural metabolite of plaque bacteria contained in dental plaque, which decalcify dental hard tissue locally and gradually.

The composition of dental plaque is approximately 80% (w/w) water, 10% plaque bacteria, 6% matrix protein and 2% extracellular polysaccharide. No method that prevents formation of dental plaque has been reported, in the presence of saliva, which always exists in the human oral cavity. When teeth are exposed to saliva, an acquired pellicle, which is a thin acellular protein film, originated from salivary glycoprotein is formed in a few minutes. This acquired pellicle always exists as long as teeth are exposed to saliva. The acquired pellicle's function is to protect teeth; however, it induces formation of dental plaque by acting as a matrix where oral bacteria attach. Bacteria adhere to the surface of teeth within several hours, and matrix protein is deposited as reversible adhesion of bacteria progresses. Extracellular polysaccharides, synthesized by plaque bacteria, are continuously deposited on the plaque matrix and this allows the dental plaque to grow.

Plaque bacteria decompose an oligosaccharide chain of glycoprotein which exist in saliva, and use this decomposition as an energy source regardless of food supply.

And a portion of the protein denatured by removing this oligosaccharide chain, incorporates into the plaque matrix. On the other hand, plaque bacteria synthesize extracellular polysaccharides by using sucrose as a major substrate when food is supplied. Extracellular polysaccharides, contained in the plaque matrix, act as an aggregating factor for some oral bacteria, and act as an energy source in case of an interruption in their regular food supply.

As mentioned above, dental plaque can be formed without food, and dental plaque progresses more when food is supplied. Dental plaque will be formed as long as saliva exists in the oral cavity. Consequently, it is important to remove dental plaque efficiently for prevention and treatment of dental caries.

The tooth, a calcified hard tissue, is not regenerated once affected by dental caries, making it very important to prevent dental caries as much as treating it. There are two ways to prevent dental caries; one is to strengthen the structure of teeth so that they may resist the attack of organic acid formed by plaque bacteria, and the other is to remove or inhibit formation of dental plaque (or, in practice, inhibit metabolism of acidogenic plaque bacteria).

Tooth brushing is the most obvious method of removing dental plaque and preventing longstanding accumulation on the surface of teeth. Unfortunately, this method does not remove enough dental plaque from the gingival margins, fissures, and contact points of teeth and cannot prevent dental caries in these regions. Thus, to resist acid attack, it is necessary to strengthen the structure of teeth in addition to tooth brushing. For this, the most prevalent method is converting hydroxyapatite [$Ca_{10}(PO_4)_6(OH)_2$], the smallest building unit of enamel apatite, into fluorapatite [$Ca_{10}(PO_4)_6F_2$] by ingesting fluoride of a suitable concentration. In some areas, the drinking water is naturally or artificially fluoridated. It is reported that the frequency of dental caries is reduced by 40~60% by water fluoridation, but it is not abolished. The structure of teeth is somewhat strengthened by fluoridation of the water supply, by topical application of fluoride and by using medicines containing fluoride. However, dental caries ultimately breaks out by continuous acid attack. Thus, it is necessary to provide an active method to inhibit or prevent organic acids which are metabolites of plaque bacteria. Although the need is great, a dental caries-inhibitor with the above-mentioned effect has not been developed yet.

Many kinds of medicine for prevention and treatment world-wide since 1970: Listerine®, which contains a phenol compound; Scope®, which contains a tertiary ammonium compound; and Peridex®, which contains chlorhexidine. However, these medicines are not effective as a dental caries-inhibitor because they mainly apply to periodontal pathogens. Listerine® and Scope® have few side effects, but their action of removing dental plaque and their antibacterial effect is not satisfying. On the other hand, Peridex® has a good effect as a medicine but has serious side effects. Ulcers of oral mucosa, exfoliating gingivitis and discoloration occur even when using a normal dose, xerostomia occurs with frequent use, and it has been reported that long term use of Peridex® may cause cancer in experimental animals. Thus, the development of a safe dental caries-inhibitor without side effects and which is usable for a long time, is an urgent matter.

The present inventor completed this invention through finding that medium-chain fatty acids have an excellent effect on inhibiting production of organic acids, growth of acidogenic plaque bacteria and synthesis of extracellular polysaccharide.

SUMMARY OF THE INVENTION

The object of the present invention is to provide use of medium-chain fatty acids as a prophylactic against dental caries and as a therapeutic treatment for the disease. A pharmaceutical composition containing medium-chain fatty acids as active ingredients of the present invention can be the best agent for prevention and treatment of dental caries.

The pharmaceutical composition containing medium-chain fatty acids as active ingredients of the present invention may include lectins and/or fluoride compound in addition to medium-chain fatty acids.

BRIEF DESCRIPTION OF THE DRAWINGS

In the accompanying figures;

FIGS. 1A to 1F represent the influence that medium-chain fatty acids have upon inhibiting acid production of cariogenic plaque bacteria (standard strains);

FIGS. 4A to 4B represent the influence that medium-chain fatty acids (1 mM of lauric acid as salt form) have upon inhibiting bacterial growth of cariogenic plaque bacteria separated from human oral cavities;
* I–X: *Lactobacillus casei*
XI–XIX: *Streptococcus mutans*
XX: *Streptococcus sobrinus*

DETAILED DESCRIPTION OF THE INVENTION

Figure 1A:
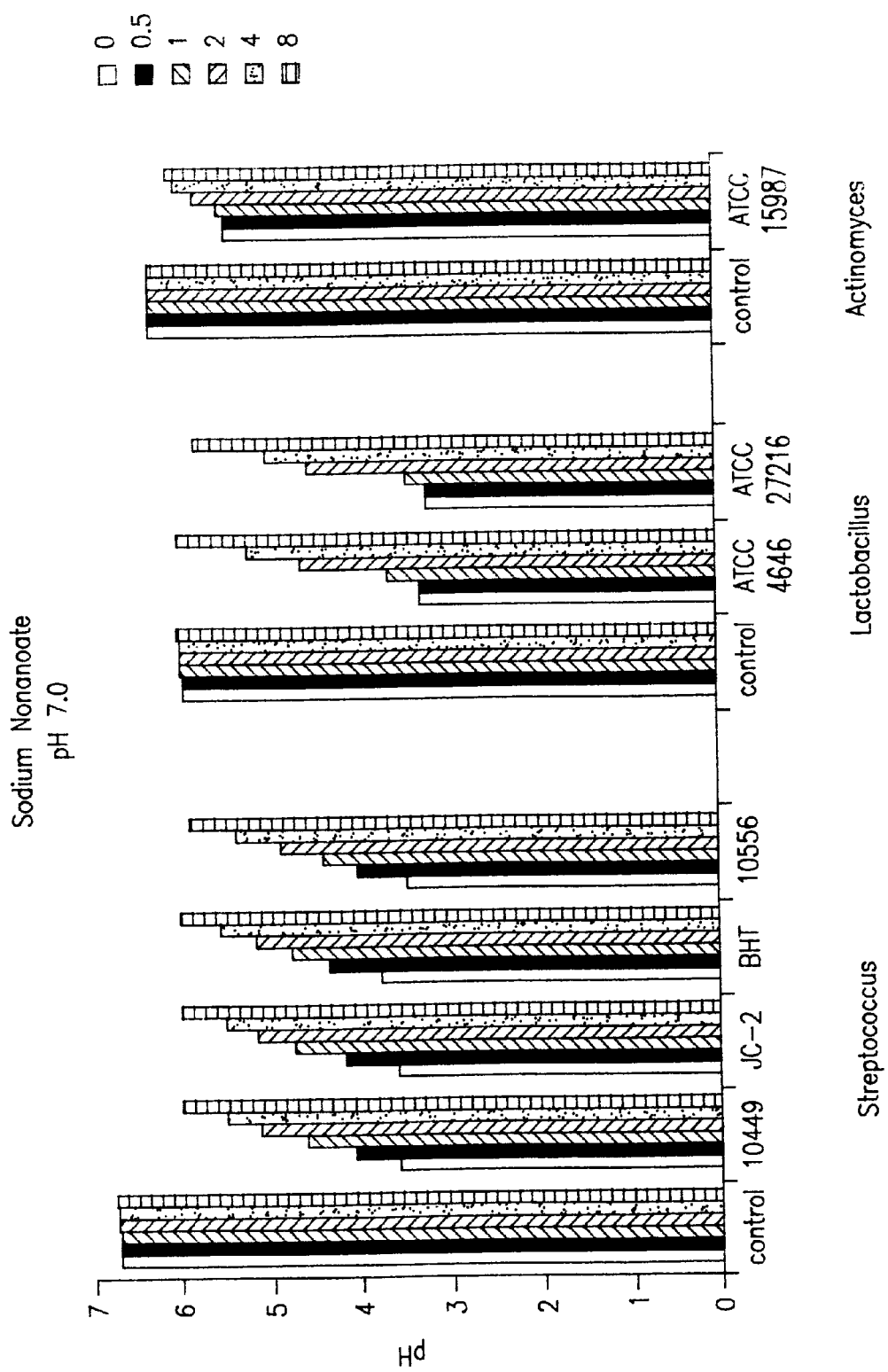
Figure 1B:
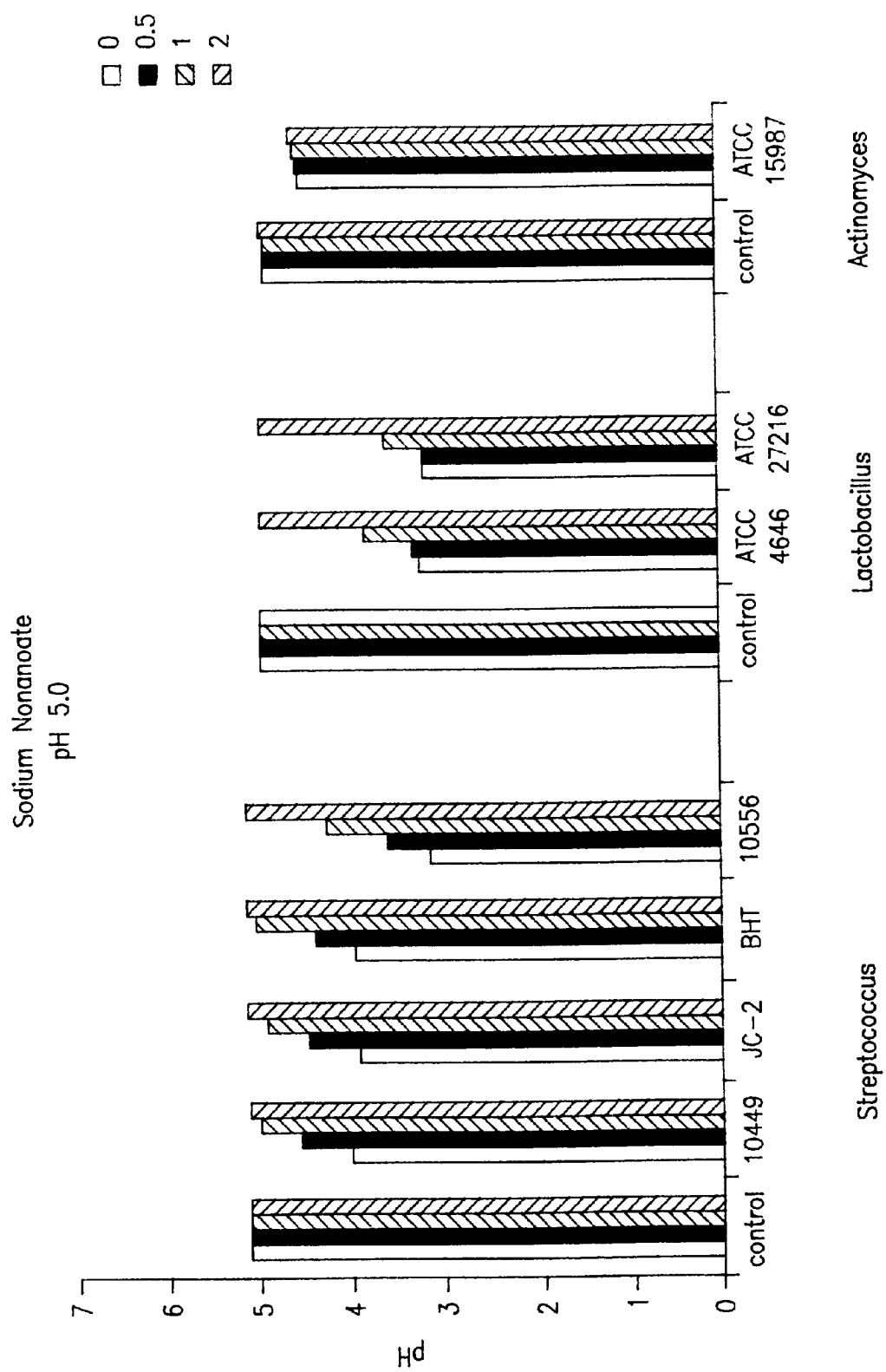
Figure 1C:
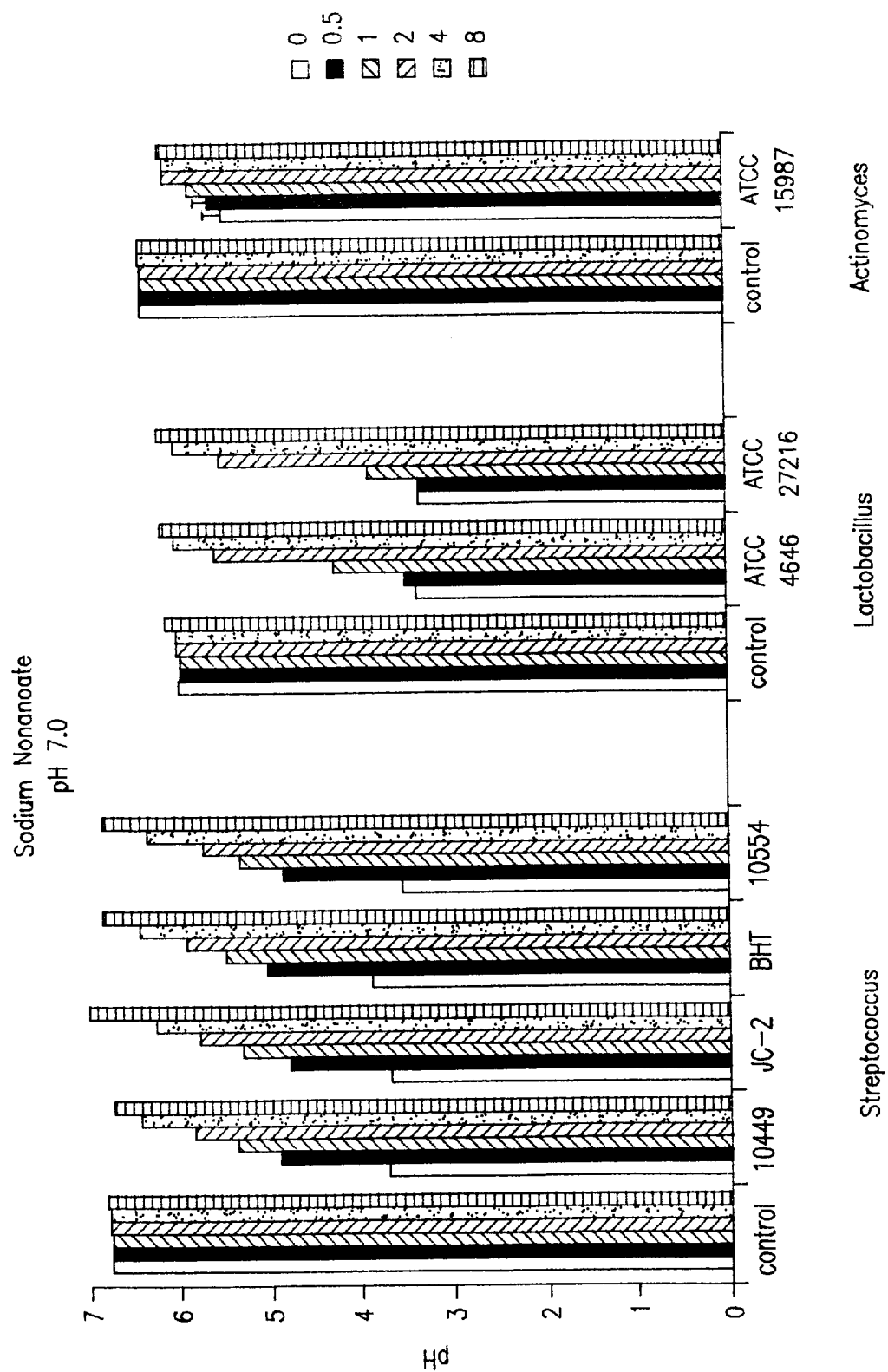
Figure 1D:
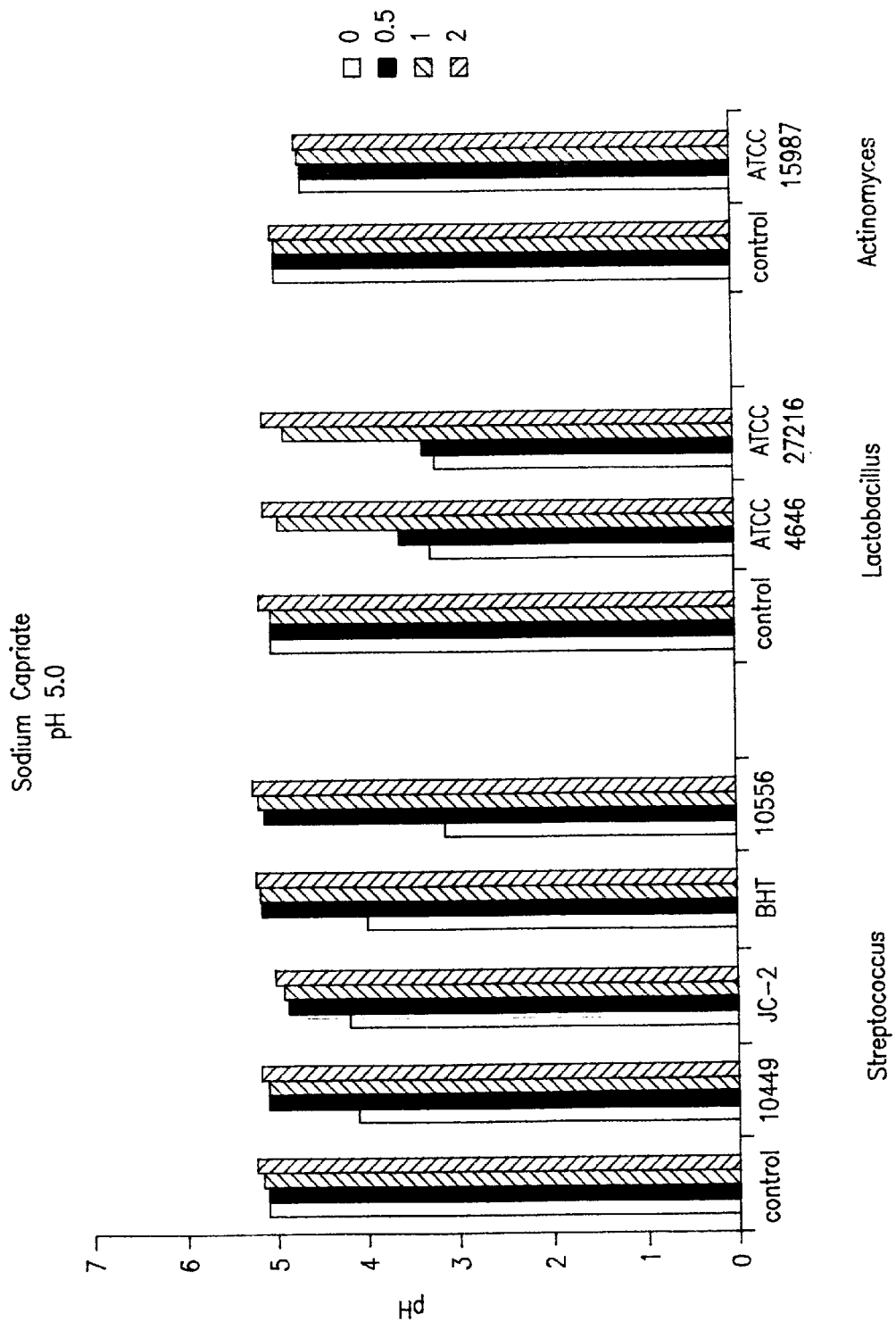

The mechanism by which fatty acids inhibit dental caries is as follows: It is known that fatty acids form a hydrophobic layer on the surface of teeth and prevent bacterial colonization by coating carbohydrates. They also inhibit reduction of pH in the affected region of dental caries by restraining production of organic acid by selectively acting on acidogenic plaque bacteria, which produce organic acids. Fatty acids also change the distribution of bacteria causing dental caries, through inhibiting proliferation of these bacteria.

It is necessary for fatty acids to pass through plaque matrix in order to inhibit acid production by acting on acidogenic plaque bacteria. However, it is difficult for fatty acids to pass through plaque matrix because they have a negative charge at physiological pH. In this invention, medium-chain fatty acids are facilitated to pass through plaque matrix by forming them as a salt. Medium-chain fatty acids inhibit acidogenic plaque bacteria from producing acids through penetrating plaque bacteria as a protonated form. Then these acids can pass through the lipid membrane by binding with a hydrogen ion which occurs as a result of carbohydrate metabolism of bacteria in the dental plaque.

In this invention, it is identified that medium-chain fatty acids are useful therapeutics for dental caries and periodontal disease through studies on inhibitory effect of acid production, bacterial growth, and extracellular polysaccharide synthesis of acidogenic plaque bacteria such as Streptococcus, Lactobacillus and Actinomyces, which are cariogenic plaque bacteria.

The result of an inhibition-effect test of acid production on the above species of acidogenic bacteria which can produce acids among plaque bacteria, shows that the salt form of medium-chain fatty acids inhibit the acid production function of all kinds of cariogenic bacteria used in this test.

The result of an inhibition-effect test of bacterial growth on cariogenic plaque bacteria, shows that the salt form of medium-chain fatty acids apparently inhibit bacterial growth of all kinds of cariogenic bacteria used in this test.

The result of an inhibition-effect test of extra-cellular polysaccharide synthesis of cariogenic plaque bacteria, shows that the salt form of medium-chain fatty acids apparently inhibit all kinds of cariogenic bacteria used in this test from synthesizing extracellular polysaccharide.

Medium-chain fatty acids of this invention include lauric acid, capric acid and nonanoic acid. These may be used independently or in combination and in their salt form. The preferable salt forms are sodium salt, potassium salt, etc.

This invention provides a pharmaceutical composition containing medium-chain fatty acids as active ingredients.

Furthermore, the remedial value of dental caries and periodontal disease increases if lectinss and/or fluoride are/is added to this pharmaceutical composition as an chemotherapeutic agent.

Lectins, glycoproteins of 17–40 kDa, are widely distributed plant constituents, found in many kinds of invertebrates and vertebrates and they are synthesized by many kinds of bacteria. Consequently, lectins are distributed widely in the biosphere. Lectins recognize specific carbohydrate units and bind to the unit, which enables them to agglutinate and inactivate glycoprotein, erythrocytes, bacteria and other cells. Due to this effect, it is reported that a number of lectins can reduce plaque formation. For example, it is reported that *Persea americana* lectin inhibits *S. mutans* 6715 from adhering to teeth. As mentioned above, it is known that lectins prevent dental caries by inhibiting plaque formation and reducing organic acid production through precipitating salivary glycoprotein. These lectins contain concanavalin A, abrin, ricin, Soybean Agglutinin and Wheat Germ Agglutinin.

Fluoride is used as a compound form in this invention. Fluoride compounds which can be used in this invention are sodium fluoride (NaF), stannous fluoride ($SnF_2$), etc.

A continuous and long-term effect of prevention and treatment for dental caries can be obtained by gargling with a liquid containing the salt form of medium-chain fatty acids used in this invention. Also, medium-chain fatty acids, formated to a solution type by mixing with normal vehicles and those contained in gum, can be used for the prevention and treatment of dental caries.

The following examples demonstrate potential applications of the present invention; however, the claims of the present invention are not limited to these examples.

EXAMPLE 1

Test on inhibitory effect of acid production of medium-chain fatty acids in cariogenic plaque bacteria In order to identify the action by which medium-chain fatty acids inhibit acid production, the inhibitory effect and concentration of acid production were determined in seven kinds of standard cariogenic plaque bacteria. Also, the inhibitory effect of acid production for 20 kinds of cariogenic plaque bacteria, separated from the human oral cavity, was assayed. Liquid culture media used were: Todd-Hewitt broth of Streptococcus, Lactobacilli MRS broth of Lactobacillus and Brain Heart Infusion broth of Actinomyces. After the pH of 2% glucose-containing culture media was adjusted to the pH 5.0 and pH 7.0, 0.1 ml of bacterial (or cell) suspension ($OD_{400}$=0.5) of each bacteria was inoculated to 5.9 ml of culture media where 0, 0.5, 1, 2, 4 and 8 mM of medium-chain fatty acids such as sodium nonanoate, sodium capriate and sodium laurate were respectively added. The final pH of the culture medium was measured after culturing for 24~48 hours in 10% $CO_2$ incubator. The result of the action and concentration that medium-chain fatty acids inhibit acid production is shown in FIG. 1.

Figure 2A:
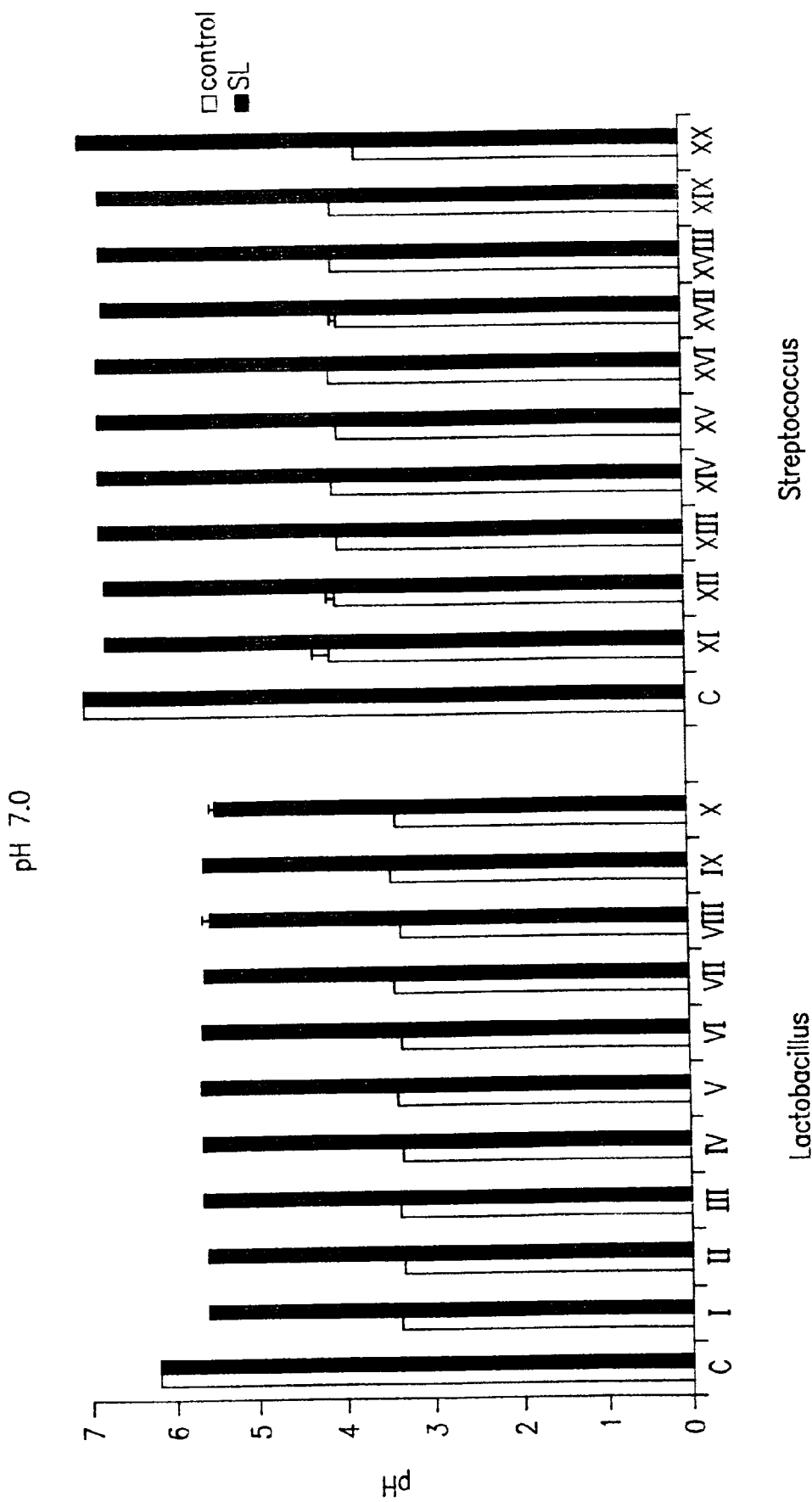
FIGS. 2A to 2B represent the influence that medium-chain fatty acids (1 mM of lauric acid as salt form) have upon inhibiting acid production of cariogenic plaque bacteria separated from human oral cavities;
* I–X: *Lactobacillus casei*
XI–XIX : *Streptococcus mutans*
XX: *Streptococcus sobrinus*
Figure 2B:
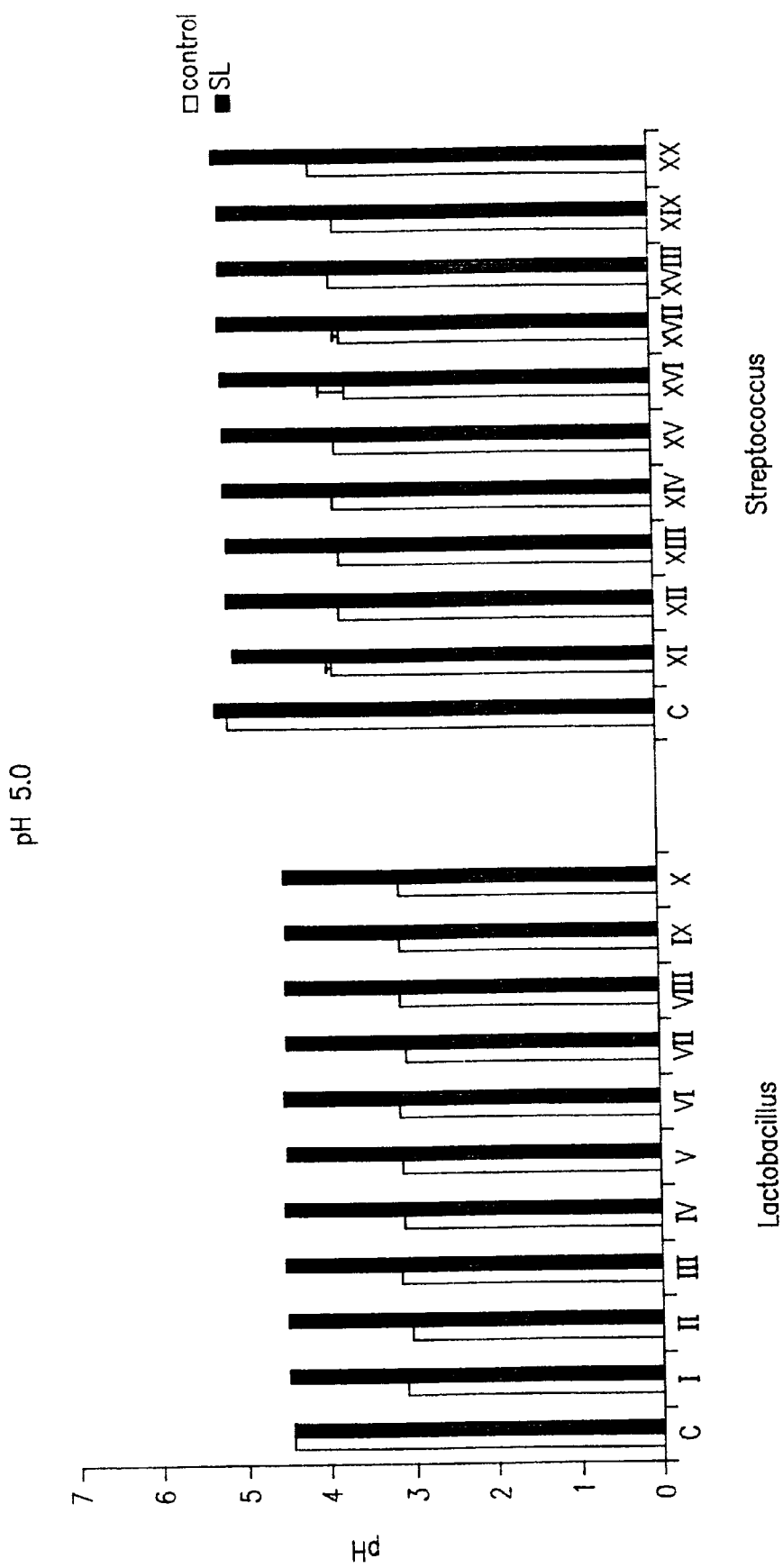
Figure 3A:
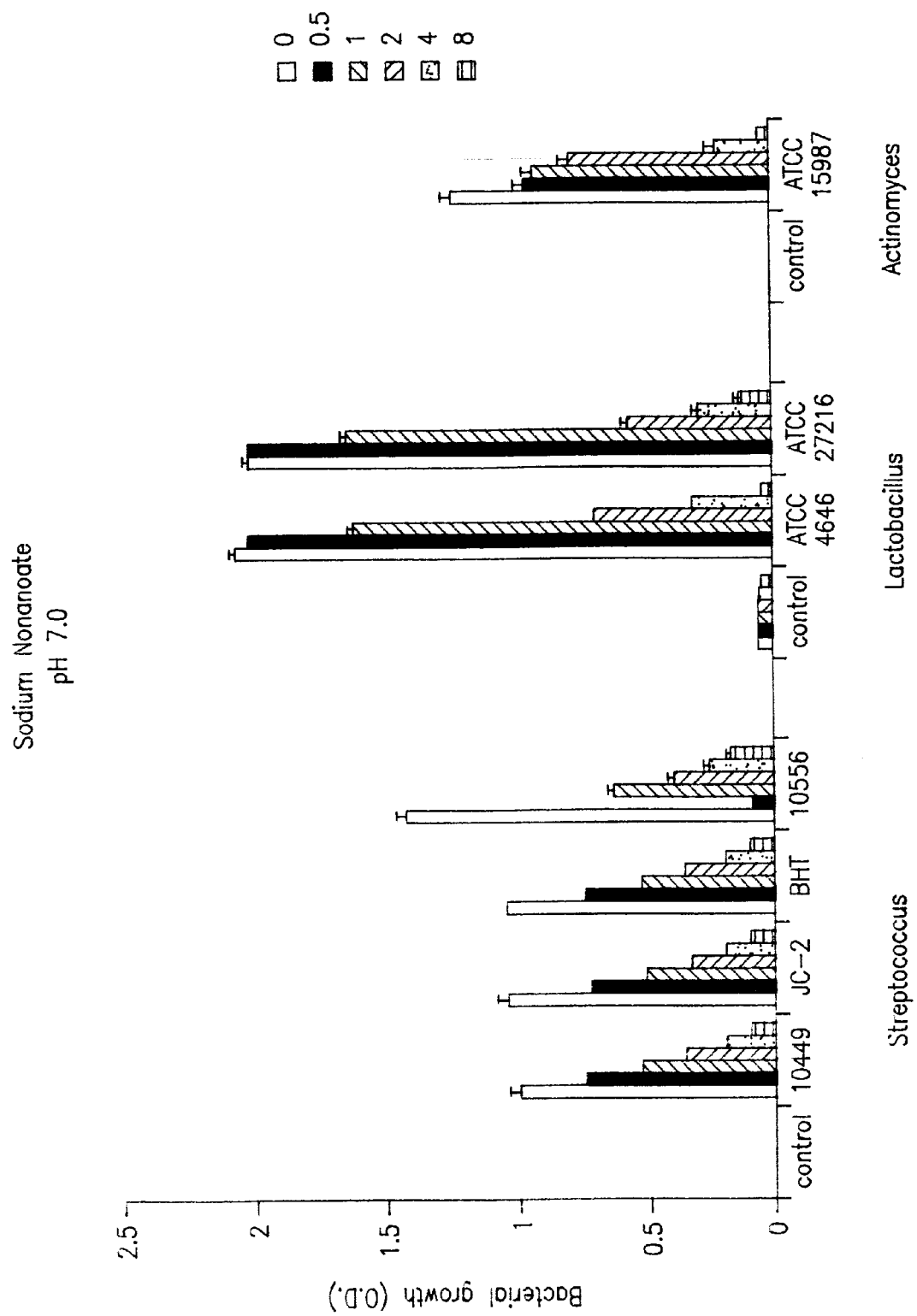
FIGS. 3A to 3F represent the influence that medium-chain fatty acids have upon inhibiting bacterial growth of cariogenic plaque bacteria (standard strains)
Figure 3B:
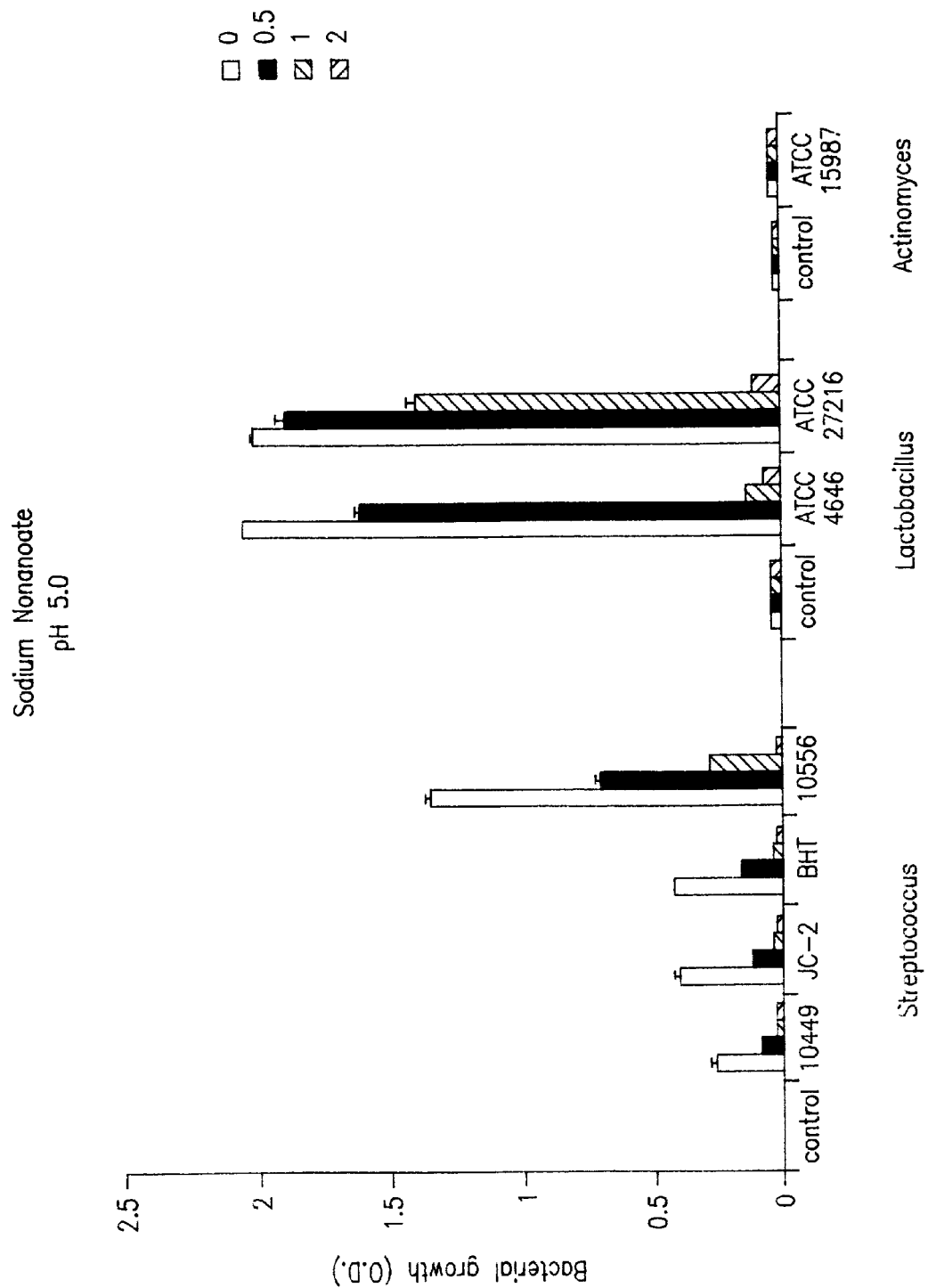
Figure 3C:
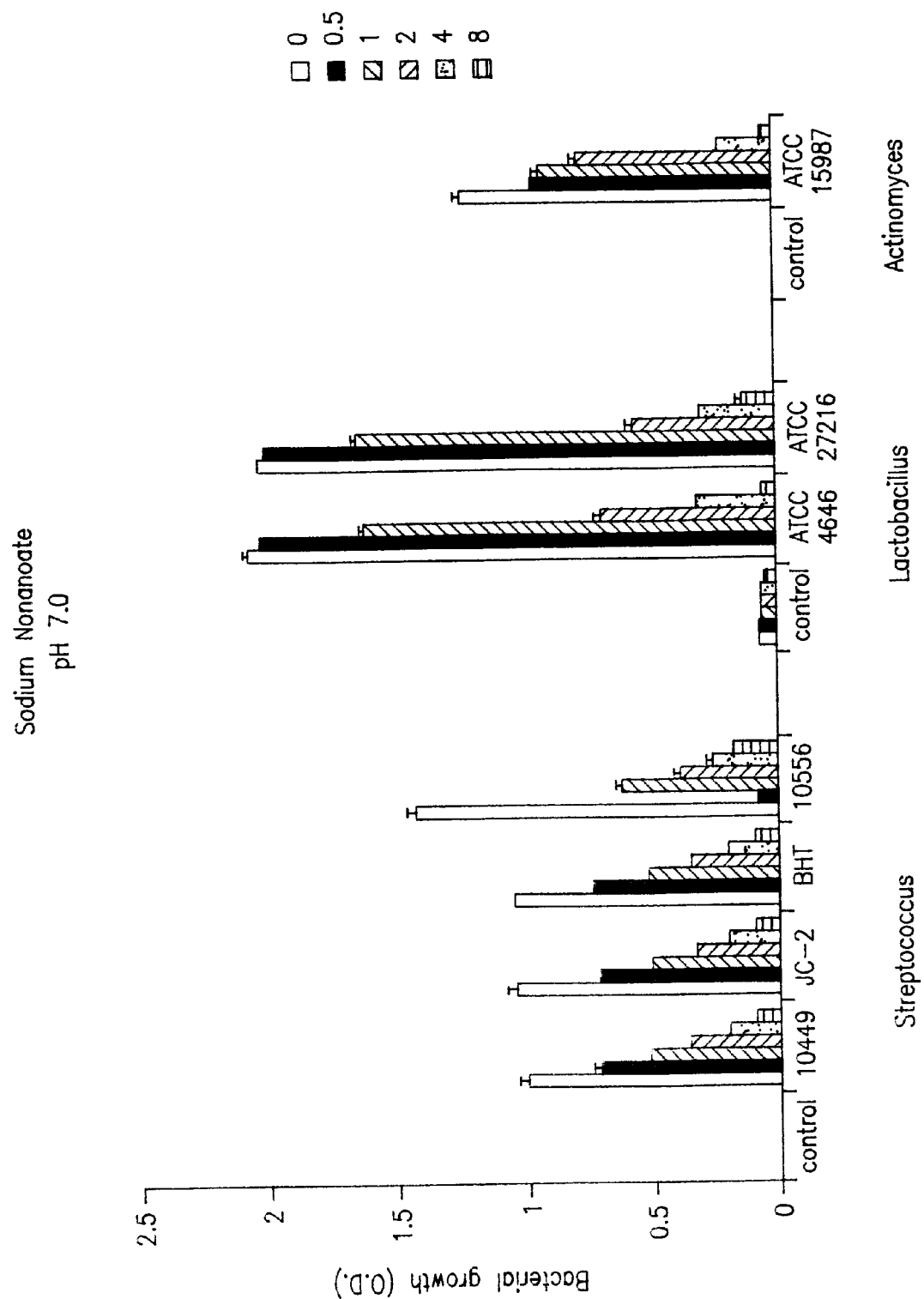
Figure 3D:
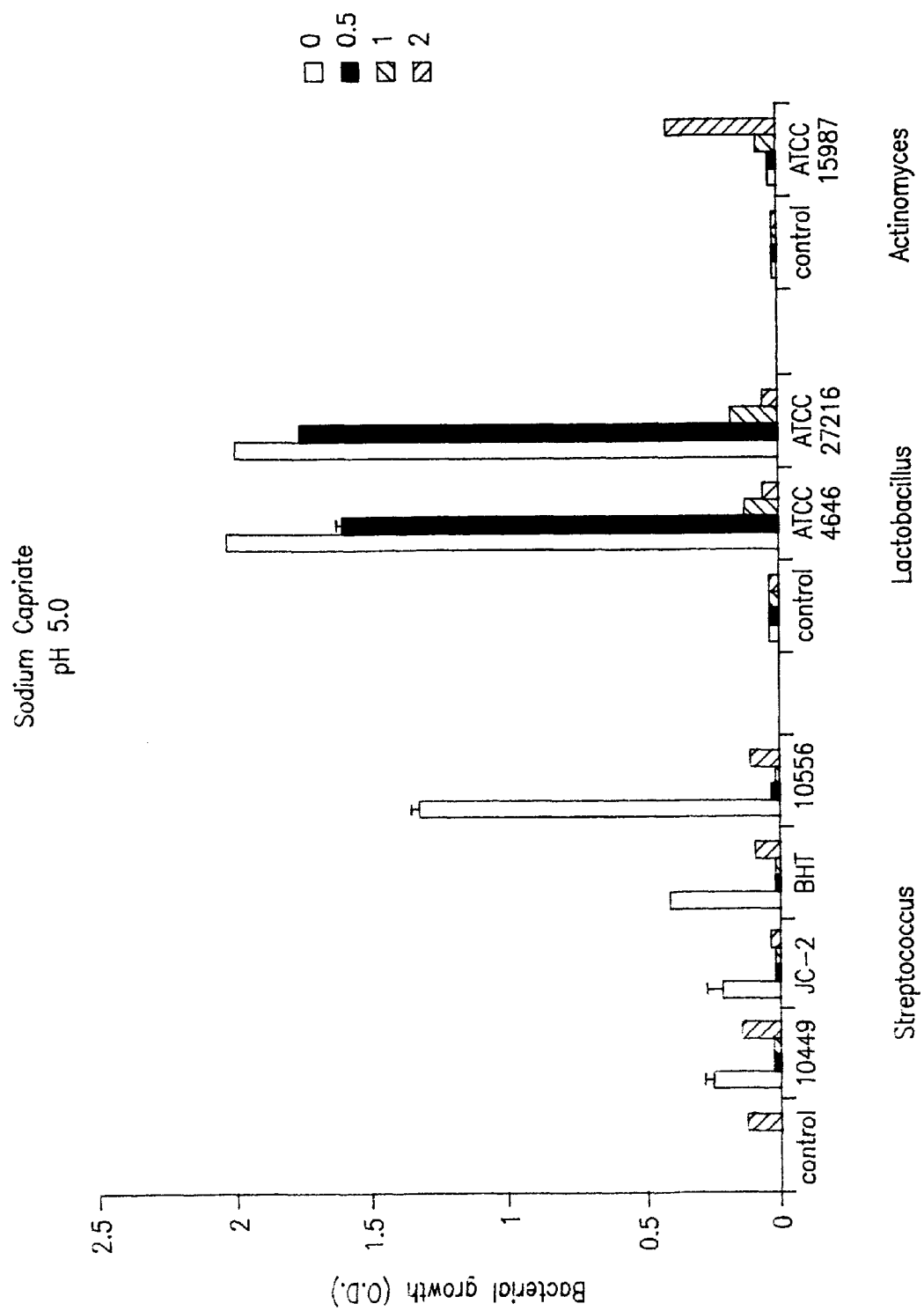
Figure 3E:
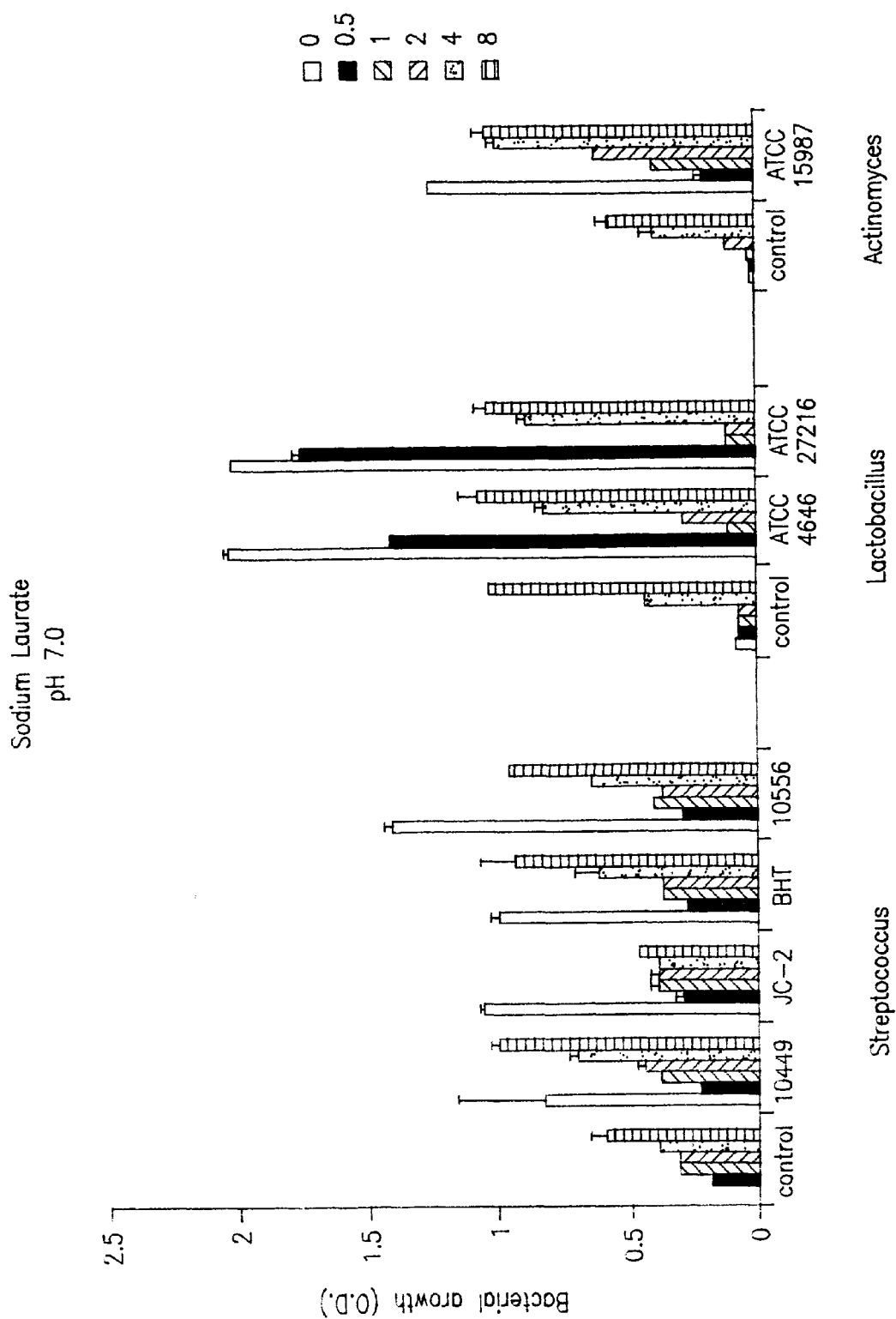
Figure 3F:
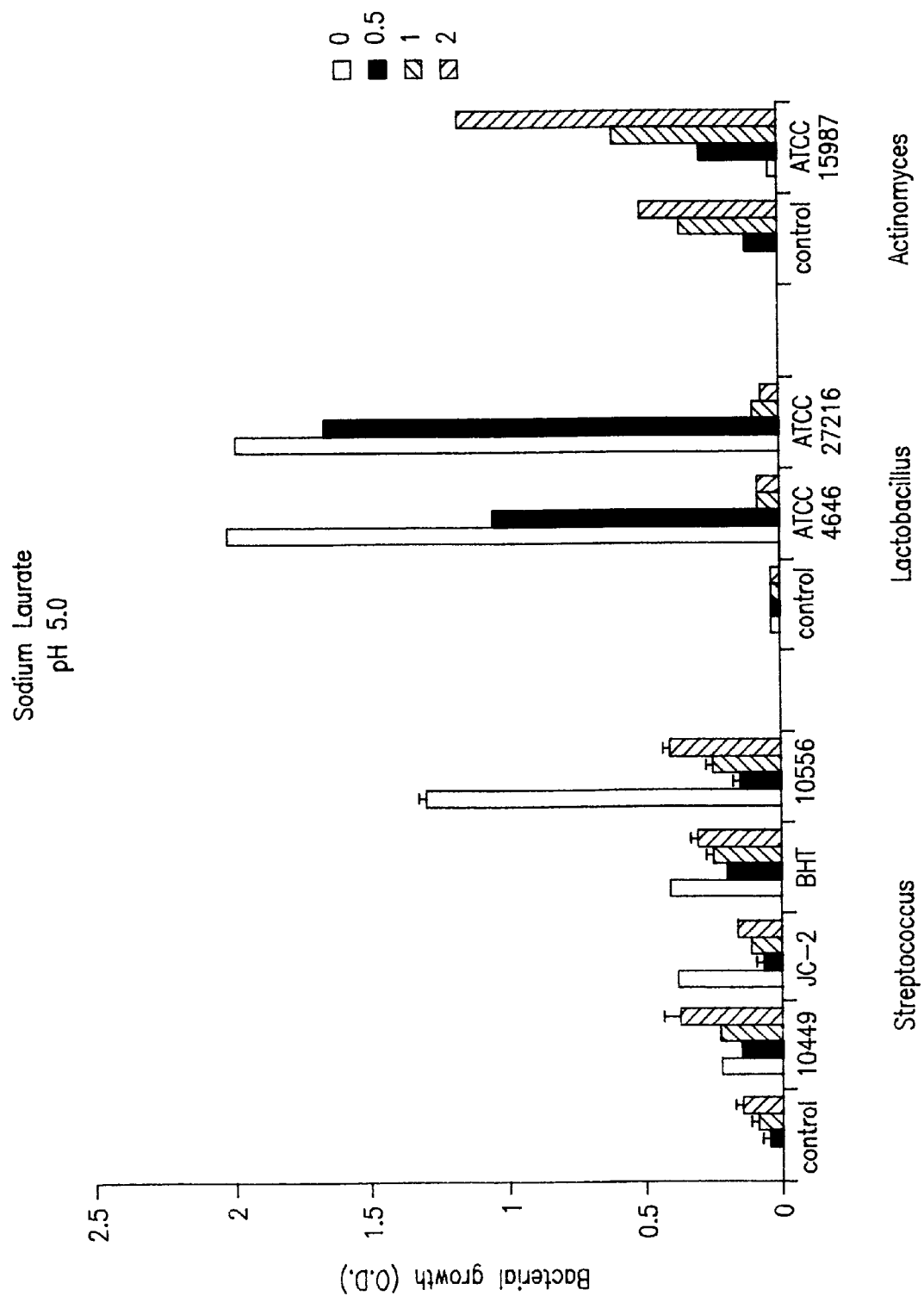

The result of the action that medium-chain fatty acids (salt form), developed in this invention, inhibit acid production upon 20 kinds of strains of cariogenic plaque bacteria (Streptococcus and Lactobacillus) which were separated and identified from the human oral cavity, is shown in FIG. 2.

As a result of the above experiment, salt form of medium-chain fatty acids inhibit the function of acid production of all kinds of cariogenic bacteria, used in this experiment. The inhibitory effect of acid production shows sodium laurate>sodium capriate>sodium nonanoate in sequence, and the effect depends on the concentration in case of the same medium-chain fatty acids. Sodium laurate, particularly, shows excellent inhibitory effect of acid production even at low concentration of 1 mM. Moreover, it shows significant effect of acid production in acidic conditions (FIG. 1).

Acid production ability of cariogenic plaque bacteria which were separated and identified from the human oral cavity, was studied in order to prove inhibitory ability as prevention and treatment of dental caries, developed in this invention. As a result of this study, these prophylactic and therapeutics inhibit acid production of all kinds of cariogenic bacteria, and meaningful inhibitory effect of acid production was obtained not only at neutral pH but also at acidic pH. Moreover, the inhibitory effect of acid production is better upon Streptococcus, which is the major cariogenic plaque bacteria, than upon Lactobacillus (FIG. 2).

EXAMPLE 2

Figure 4A:
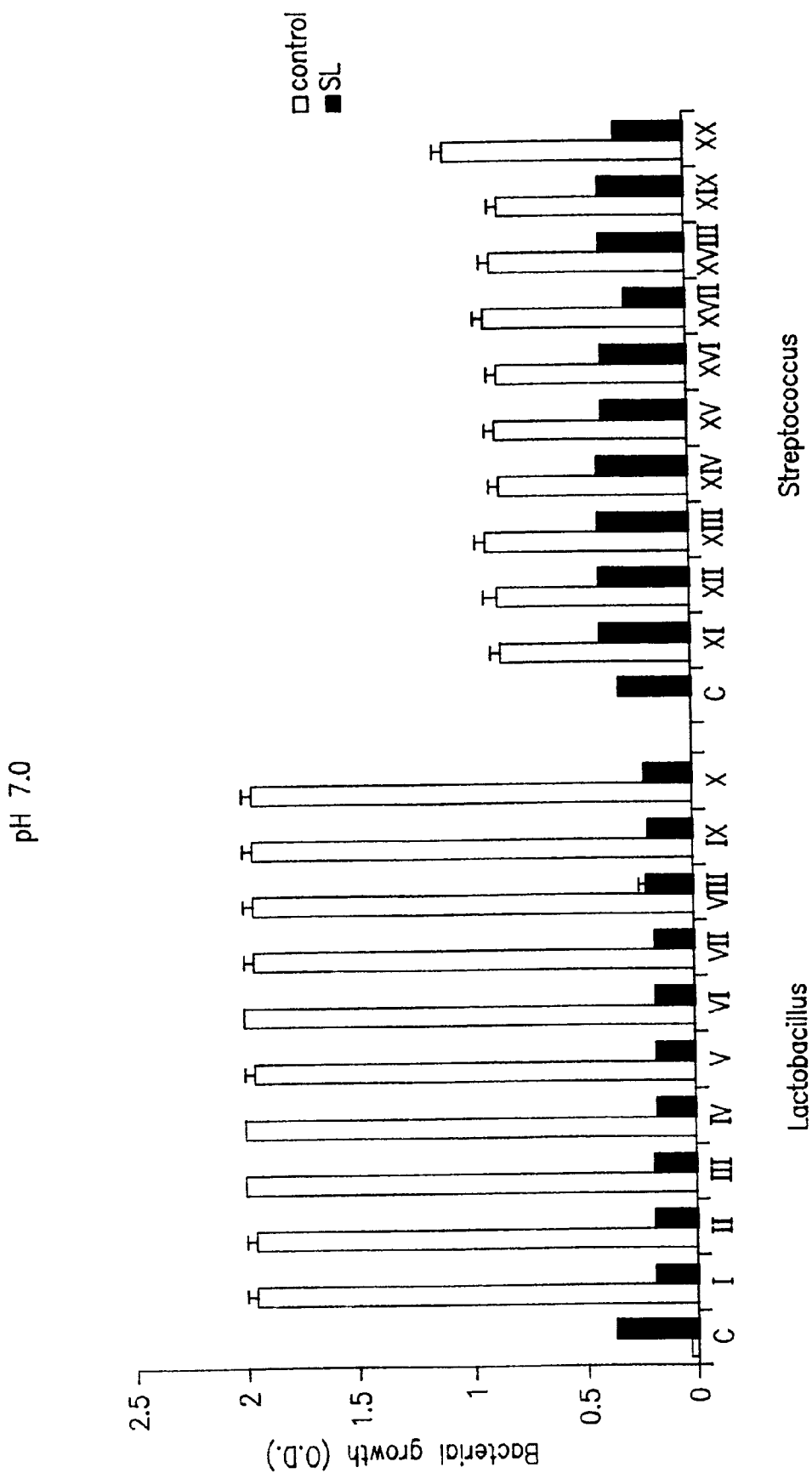

Test on inhibitory effect of bacterial growth of medium-chain fatty acids in cariogenic plaque bacteria In order to evaluate how medium-chain fatty acids influence bacterial growth of cariogenic plaque bacteria, the influence on each bacteria was evaluated after selecting seven kinds of bacterial strains as standard bacteria among cariogenic plaque bacteria. After pH of 2% glucose-containing culture media were adjusted to pH 5.0 and pH 7.0, 0.1 ml of bacterial suspension ($OD_{600}$=0.5) of each bacteria was inoculated to 5.9 ml of culture medium where 0, 0.5, 1, 2, 4 and 8 mM of medium-chain fatty acids such as sodium nonanoate, sodium capriate and sodium laurate were respectively added, turbidity of bacteria was determined by measuring optical density at 600 nm after culturing for 24–48 hours in 10% $CO_2$ incubator. The results that medium-chain fatty acids have on influencing bacterial growth of cariogenic plaque bacteria is shown in FIG. 3. And the result of measuring inhibitory effect of bacterial growth of 20 kinds of cariogenic plaque bacteria separated from the human oral cavities is shown in FIG. 4.

As a result of the above experiment, the salt form of medium-chain fatty acids inhibited bacterial growth of all kinds of cariogenic bacteria, used in this experiment, and inhibitory effect of bacterial growth showed sodium laurate>sodium capriate>sodium nonanoate in sequence. Particularly, the more the number of carbon the medium-chain fatty acids have, the better inhibitory effect of bacterial growth is obtained even at low concentration (1 mM), and this effect is good even in acidic conditions (FIG. 3).

The influence upon bacterial growth of cariogenic plaque bacteria, separated and identified from human oral cavities was studied in order to examine inhibitory ability of plaque formation for pharmaceutical composition developed in this invention. This composition inhibited bacterial growth of all kinds of bacteria extremely well. This inhibitory effect was good not only at neutral pH but also at acidic pH and better upon Streptococcus than upon Lactobacillus. That is, the salt form of lauric acid shows more remarkable effects even at low concentration than that of the control group, and this shows that salt form of lauric acid inhibits plaque formation through inhibiting bacterial growth of plaque bacteria which is a major component of dental plaque (FIG. 4).

EXAMPLE 3

Test on inhibitory effect of extracellular polysaccharide synthesis of medium-chain fatty acids in cariogenic plaque bacteria In order to identify the effect by which medium-chain fatty acids inhibit plaque matrix formation, inhibitory effect and concentration of extracellular polysaccharide synthesis were determined in seven kinds of standard cariogenic plaque bacteria. Also, the inhibitory effect of extracellular polysaccharide synthesis for 20 kinds of cariogenic plaque bacteria, separated from the human oral cavity, was measured. Liquid culture media used were: Todd-Hewitt broth of Streptococcus, Lactobacilli MRS broth of Lactobacillus and Brain Heart Infusion broth of Actinomyces. 0.1 ml of bacterial (or cell) suspension ($OD_{600}$=0.5) of each bacteria was inoculated to 5.9 ml of culture media containing 1 mM of medium-chain fatty acids and 2% of glucose, and was cultured for 24~48 hours in 10% $CO_2$ incubator. After culturing, the resultant was centrifuged to precipitate at 5,000×g for 15 minutes, then soluble extracellular polysaccharide was separated and purified from the supernatant and insoluble extracellular polysaccharide from the cell pellet, and then these were quantified. So the experimental results that represent inhibitory effect of medium-chain fatty acids upon extracellular polysaccharide synthesis, are shown in table 1, 2, 3 and 4.

TABLE 1

Effect on extracellular polysaccharide synthesis of medium-chain fatty acids in standard strains of Streptococcus among cariogenic bacteria

| Group | Extracellular polysaccharide ($\mu$g/ml) | | Inhibitory rate (%) |
|---|---|---|---|
| | soluble | insoluble | soluble |
| Control group (liquid medium) | 1.8 ± 0.3 | 0 | — |
| $C_9$ (sodium nonanoate) | 2.0 ± 0.7 | 0 | — |
| $C_{10}$ (sodium capriate) | 0.7 ± 0.4 | 0 | — |
| $C_{12}$ (sodium laurate) | 1.4 ± 0.1 | 0 | — |
| S. mutans 10449 | 74.6 ± 1.8 | 0.8 ± 0.3 | 0 |
| S. mutans 10449 + $C_9$ | 50.8 ± 12.2 | 0.6 ± 0.2 | 32 |
| S. mutans 10449 + $C_{10}$ | 19.6 ± 2.3 | 0.4 ± 0.1 | 74 |
| S. mutans 10449 + $C_{12}$ | 15.5 ± 3.8 | 0.2 ± 0.1 | 79 |
| S. mutans JC-2 | 34.4 ± 3.9 | 1.1 ± 0.2 | 0 |
| S. mutans JC-2 + $C_9$ | 6.2 ± 3.5 | 0.9 ± 0.3 | 82 |
| S. mutans JC-2 + $C_{10}$ | 4.4 ± 1.1 | 0.3 ± 0.1 | 87 |
| S. mutans JC-2 + $C_{12}$ | 0.6 ± 0.5 | 0.1 ± 0.1 | 98 |
| S. mutans BHT | 31.5 ± 3.7 | 0.5 ± 0.1 | 0 |
| S. mutans BHT + $C_9$ | 8.0 ± 1.1 | 0.3 ± 0.1 | 75 |
| S. mutans BHT + $C_{10}$ | 5.1 ± 1.7 | 0 | 84 |
| S. mutans BHT + $C_{12}$ | 4.1 ± 0.8 | 0 | 87 |
| S. sanguis 10556 | 25.9 ± 4.3 | 0.6 ± 0.3 | 0 |
| S. sanguis 10556 + $C_9$ | 17.4 ± 8.9 | 0.5 ± 0.2 | 33 |
| S. sanguis 10556 + $C_{10}$ | 11.7 ± 1.7 | 0.3 ± 0.2 | 55 |
| S. sanguis 10556 + $C_{12}$ | 12.2 ± 0.9 | 0 | 53 |

TABLE 2

Effect on extracellular polysaccharide synthesis of medium-chain fatty acids in standard strains of Lactobacillus among cariogenic bacteria

| Group | Extracellular polysaccharide ($\mu$g/ml) | | Inhibitory rate (%) |
|---|---|---|---|
| | soluble | insoluble | soluble |
| Control group (liquid medium) | 5.0 ± 1.5 | 0 | — |
| $C_9$ (sodium nonanoate) | 4.6 ± 0.2 | 0 | — |
| $C_{10}$ (sodium capriate) | 3.9 ± 0.9 | 0 | — |
| $C_{12}$ (sodium laurate) | 4.6 ± 1.3 | 0 | — |
| L. casei ATCC 4646 | 43.6 ± 7.0 | 5.3 ± 0.5 | 0 |
| L. casei ATCC 4646 + $C_9$ | 31.9 ± 4.0 | 3.8 ± 0.5 | 27 |
| L. casei ATCC 4646 + $C_{10}$ | 25.7 ± 2.8 | 0.3 ± 0.2 | 41 |
| L. casei ATCC 4646 + $C_{12}$ | 19.2 ± 2.9 | 0.2 ± 0.2 | 56 |
| L. casei ATCC 27216 | 67.3 ± 4.5 | 5.9 ± 0.4 | 0 |
| L. casei ATCC 27216 + $C_9$ | 70.1 ± 3.3 | 5.1 ± 0.5 | 4 (increase) |
| L. casei ATCC 27216 + $C_{10}$ | 40.7 ± 5.4 | 2.0 ± 0.2 | 40 |
| L. casei ATCC 27216 + $C_{12}$ | 19.0 ± 2.1 | 2.0 ± 0.1 | 72 |

TABLE 3

Effect on extracellular polysaccharide synthesis of medium-chain fatty acids in standard strains of Actinomyces among cariogenic bacteria

| Group | Extracellular polysaccharide ($\mu$g/ml) | | Inhibitory rate (%) |
|---|---|---|---|
| | soluble | insoluble | soluble |
| Control group (liquid medium) | 8.5 ± 0.4 | 0 | — |
| $C_9$ (sodium nonanoate) | 8.2 ± 0.4 | 0 | — |
| $C_{10}$ (sodium capriate) | 8.5 ± 0.5 | 0 | — |
| $C_{12}$ (sodium laurate) | 4.4 ± 0.2 | 0 | — |
| A. viscosus ATCC 15987 | 222.8 ± 3.3 | 2.1 ± 0.2 | 0 |
| A. viscosus ATCC 15987 + $C_9$ | 241.6 ± 3.9 | 1.4 ± 0.5 | 8 (increase) |
| A. viscosus ATCC 15987 + $C_{10}$ | 98.1 ± 6.5 | 0.2 ± 0.2 | 56 |
| A. viscosus ATCC 15987 + $C_{12}$ | 25.3 ± 1.7 | 0.2 ± 0.1 | 89 |

TABLE 4

Effect on extracellular polysaccharide synthesis of salt form of lauric acid in cariogenic plaque bacteria separated from human oral cavities

| | Soluble extracellular polysaccharide ($\mu$g/ml) | | Inhibitory rate (%) |
|---|---|---|---|
| | control group | lauric acid | |
| I | 105.1 ± 7.2 | 25.1 ± 1.7 | 76 |
| II | 121.4 ± 27.1 | 35.0 ± 2.9 | 71 |
| III | 140.4 ± 4.9 | 34.7 ± 0.9 | 75 |
| IV | 151.4 ± 7.6 | 38.8 ± 4.1 | 74 |
| V | 137.4 ± 21.8 | 36.6 ± 4.3 | 73 |
| VI | 184.6 ± 6.5 | 48.5 ± 2.7 | 74 |
| VII | 149.9 ± 16.8 | 44.7 ± 3.1 | 70 |
| VIII | 221.6 ± 20.1 | 62.6 ± 3.4 | 72 |
| IX | 214.6 ± 18.8 | 46.1 ± 3.0 | 79 |
| X | 201.7 ± 36.1 | 56.3 ± 8.2 | 72 |
| XI | 95.2 ± 8.3 | 28.6 ± 3.5 | 70 |
| XII | 84.2 ± 8.6 | 35.2 ± 5.0 | 58 |
| XIII | 90.5 ± 8.3 | 27.7 ± 3.3 | 69 |
| XIV | 90.5 ± 2.9 | 42.6 ± 1.0 | 53 |
| XV | 117.5 ± 4.6 | 44.5 ± 1.7 | 62 |
| XVI | 143.2 ± 11.1 | 48.2 ± 4.5 | 66 |
| XVII | 107.8 ± 17.0 | 35.4 ± 2.1 | 67 |
| XVIII | 98.5 ± 9.0 | 40.5 ± 1.7 | 59 |
| XIX | 113.7 ± 6.8 | 34.3 ± 3.3 | 70 |
| XX | 116.0 ± 17.2 | 24.0 ± 1.5 | 79 |

I ~ X : *Lactobacillus casei*
XI ~ XIX : *Streptococcus mutans*
XX : *Streptococcus sobrinus*

Major extracellular polysaccharide synthesized from all kinds of cariogenic plaque bacteria used in the experiment was soluble extracellular polysaccharide, and insoluble extracellular polysaccharide was synthesized only in a small amount. When 1 mM of sodium nonanoate was added, synthesis of soluble extracellular polysaccharide was inhibited in the case of Streptococcus, by 32~82%, compared with the control group, and 55~87% in the case of sodium capriate, and 53~98% in the case of sodium laurate (Table 1). In the case of Lactobacillus, synthesis of soluble extracellular polysaccharide was similar to that of the control group, or reduced by 27% compared with the control group when 1 mM of sodium nonanoate was added, which is somewhat different according to strains, but the synthesis was inhibited by 40~41% in the case of sodium capriate, and 56~72% in the case of sodium laurate (Table 2). In the case of Actinomyces, synthesis of soluble extracellular polysaccharide was increased by 8% compared with the control group when 1 mM of sodium nonanoate was added, but inhibited by 56% in the case of sodium capriate, and 89% in the case of sodium laurate (Table 3). And synthesis of insoluble extracellular polysaccharide was greatly reduced compared with the control group when 1 mM of medium-chain fatty acids was added, though it was synthesized in a small amount.

As a result of the above experiment, the salt form of medium-chain fatty acids inhibit extracellular polysaccharide synthesis of almost all kinds of cariogenic plaque bacteria used in this experiment, and the inhibitory effect of extracellular polysaccharide synthesis shows sodium laurate>sodium capriate>sodium nonanoate in sequence. Particularly, soluble and insoluble extracellular polysaccharide synthesis was inhibited in the highest degree when sodium laurate was added Also, sodium laurate of low concentration (1 mM) noticeably inhibits soluble extracellular polysaccharide synthesis of 20 kinds of cariogenic plaque bacteria separated from human oral cavities (Table 4). These results show that medium-chain fatty acids have the effect of preventing formation of dental plaque through inhibiting extracellular polysaccharide (major component of dental plaque) synthesis.

EXAMPLE 4

Inhibitory effect of medium-chain fatty acids on the occurrence of dental caries in rats This experiment was carried out utilizing a dental caries experiment model in rats of Navia (1977) as followings.

1) Experimental animal

Experimental animals were 48 (male: 24, female: 24) Sprague-Dawley rats, four-weeks old and of 200±0 mg average body weight. These animals are equally divided into three groups according to sex and body weight at the early stage, and all these animals have clinically healthy teeth.

2) Method for the experiment

Experimental animals are divided into 3 groups according to diet, which are a control group of normal feed, a group of dental caries-induced feed and a experimental group of sodium laurate-added feed. Normal feed is solid feed for rodents (SAMYANG Co., Korea), caries-induced feed is prepared by mixing 40% sugar, 32% powdered milk, 21% flour, 5% yeast, 2% anchovy, 0.01% vitamin B and 0.01% vitamin C. Sodium laurate-added feed was prepared by adding 50 mM of sodium laurate to caries-induced feed. All the experimental animals were allowed water ad libitum.

One hundred twenty days later, all experimental animals were euthanized. The maxilla and mandible were separated, and fixed in 10% neutral formalin. A dental caries index was measured by the method originated by Keyes and modified by Larson (1981). Food debris remaining in the fissure of molar of maxilla and mandible was removed by a Barbed Broach tool used in clinical dentistry, then the molar teeth of maxilla and mandible were cut so that they could include the first, second, and third molar by using an Exact cutting system (Exact-Apprateb, Hamburg, Germany) equipped with a diamond-treated saw. Cutting of the molar teeth of both maxilla and mandible was carried out by a handpiece equipped with cutting disc (thickness, 0.004 inch; diameter, 0.75 inch). The direction of the cutting was from the mesial side of the first molar to the distal side of the third molar. The samples which were cut were stained in order to measure the dental caries-index easily. Staining was carried out as follows; samples were cultured with 0.02% solution of ammonium prupurate (murexide) for 12 hours, washed with flowing water for 10 minutes, then treated with 0.2% of ammoniacal silver nitrate for 30 seconds and washed with flowing water for 2 minutes before measurement. The degree of the affection of dental caries at the cut surface is classified into enamel only (E) when dental caries is affected only to enamel; and into slight (Ds), moderate (Dm) and extensive (Dx) according to the extent of affection when dental caries is affected further into the dentine. The total sum was calculated by adding up marks within the range of linear units administered to each tooth according to the modified method of Larson (1981). This was observed with optical microscope (Olympus BH-2, Olympus Co., Tokyo, Japan) in wet samples.

3) Statistical Analysis

Statistical analysis of each group concerning the linear unit, showing the extent of dental caries, was carried out using the Mann-Whitney test. Statistical analysis according to the feed and the region where the teeth were placed (maxilla or mandible) was carried out by the Kruskal-Wallis test. If more than ⅔ of the dental crown was lost due to serious abrasion and if it was impossible to observe in the process of treating samples, these teeth were excluded in the statistics.

4) Result of Experiment

Table 5 shows sum, average and standard deviation of linear unit of fissure-region dental caries for the first, second and third molars of rats in groups of normal feed, dental caries-inducing feed and sodium laurate-added feed. Table 6 shows the average and standard deviation of linear unit of fissure-region dental caries according to the region where the teeth were placed.

TABLE 5

Linear unit for fissure-region dental caries according to diet

| Groups | molar | Maxilla | | | | molar | Mandible | | | | Total numbers of teeth | Linear unit average ± standard deviation) |
|---|---|---|---|---|---|---|---|---|---|---|---|---|
| | | E | Ds | Dm | Total(n) | | E | Ds | Dm | Total(n) | | |
| Normal feed | 1st | 52 | 5 | 0 | 57(23) | 1st | 68 | 4 | 0 | 72(16) | 128 | 2.34 ± 1.37 |
| | 2nd | 40 | 3 | 0 | 43(23) | 2nd | 67 | 7 | 0 | 74(22) | | |
| | 3rd | 28 | 0 | 0 | 28(23) | 3rd | 24 | 1 | 0 | 25(21) | | |
| Caries-inducing feed | 1st | 86 | 0 | 0 | 86(26) | 1st | 108 | 33 | 5 | 146(28) | 164 | 3.01 ± 2.35* |
| | 2nd | 54 | 1 | 0 | 55(27) | 2nd | 91 | 26 | 4 | 121(28) | | |
| | 3rd | 40 | 0 | 0 | 40(27) | 3rd | 39 | 5 | 1 | 45(28) | | |
| Sodium laurate-added feed | 1st | 61 | 1 | 0 | 62(29) | 1st | 72 | 7 | 0 | 79(26) | 164 | 1.71 ± 1.26** |
| | 2nd | 41 | 0 | 0 | 41(29) | 2nd | 55 | 10 | 0 | 65(26) | | |
| | 3rd | 17 | 0 | 0 | 17(29) | 3rd | 16 | 0 | 0 | 16(25) | | |

1) E:case that dental caries is affected only to enamel
2) according to extent of affection in case that dental caries is affected to dentine; Ds:slight, Dm:moderate
3) *:statistical significance of each group for group of normal feed (P < 0.01)
**:statistical significance of each group for group of dental caries-inducing feed (P < 0.01)

TABLE 6

Linear unit for fissure-region dental caries according to region where the teeth were placed

| | number of teeth | Linear unit (average ± standard deviation) | statistical significance |
|---|---|---|---|
| Maxilla | 311 | 1.73 ± 1.07 | P < 0.05 |
| Mandible | 303 | 2.73 ± 2.10 | |

The group of caries-inducing feed has the highest average value of linear unit among each group according to feed, and the group of sodium laurate-added feed has the lowest. This demonstrates that sodium laurate noticeably reduced dental caries in experimental animals (Table 5). The sodium laurate-added group compared with the group of normal feed and caries-inducing feed, shows significant statistical difference among each group according to feed. The linear unit for fissure-region dental caries according to the region where the teeth were placed is much higher in maxilla than in mandible. It is known that dental caries frequently occurs in the mandible of rats (Table 6).

The present invention is embodied in the following preparation examples, but the claims of the present invention is not limited to these examples. These preparation examples can be variously modified in the range of this invention.

PREPARATION EXAMPLE 1

Solution type composition

| ethyl alcohol | 11.5 % w/w |
| --- | --- |
| peppermint oil | 0.06 % w/w |
| lauric acid (salt form) | 0.3 % w/w |
| distilled water | 88.14 % w/w |

Solution type composition is prepared by mixing and solubilizing the above components by the normal preparation method of solution type composition, and by adjusting the pH of this solution to 7.0. Dental caries can be prevented and treated by gargling with this solution twice or thrice a day. Also, gingivitis and periodontal disease may be prevented, too.

PREPARATION EXAMPLE 2

Medicated toothpaste composition

| abrasive; alumina | 25 % w/w |
| --- | --- |
| moisturizing agent; propylene glycol | 30 % w/w |
| binding agent; SCMC | 2 % w/w |
| aspartam | 0.3 % w/w |
| peppermint | 0.5 % w/w |
| lauric acid (salt form) | 0.3 % w/w |
| distilled water | 41.9 % w/w |

Medicated toothpaste composition is prepared by mixing the above components by the normal preparation method of toothpaste. Dental caries can be prevented and treated by tooth brushing with this toothpaste. Also, gingivitis and periodontal disease may be prevented, too.

PREPARATION EXAMPLE 3

Medicated gum composition

| chicle | 25 % w/w |
| --- | --- |
| softening agent | 0.1 % w/w |
| lauric acid (salt form) | 0.3 % w/w |
| saccharide | 72.7 % w/w |
| spice | 1.9 % w/w |

Medicated gum composition is prepared by mixing the above components by the normal preparation method of gum. Dental caries can be prevented and treated by chewing this gum. Also, gingivitis and periodontal disease may be prevented, too.

PREPARATION EXAMPLE 4

Spray type composition

| lauric acid (salt form) | 2.2 % w/w |
| --- | --- |
| trichloromonofluoromethane | 43.8 % w/w |
| dichlorodifluoromethane | 45 % w/w |
| peppermint oil | 0.1 % w/w |
| ethanol | 6 % w/w |
| polyethylene glycol | 2.9 % w/w |

Spray type composition is prepared by mixing the above components by the normal preparation method of spray type composition, and by filling it up and packing it in a compressed vessel. Dental caries can be prevented and treated by spraying and applying this composition to the surface of the teeth and the gingival region. Also, gingivitis and periodontal disease may be prevented, too.

PREPARATION EXAMPLE 5

Composition of nonanoic acid and capric acid

The compositions mentioned in examples 1–4 can be prepared to contain the salt form of nonanoic acid and capric acid as an active ingredient instead of the salt form of lauric acid. The salt form of lauric acid is replaced by the salt form of 0.3% (w/w) nonanoic acid and capric acid.

EFFECT OF THE INVENTION

Medium-chain fatty acids have a very remarkable effect on inhibiting acid production, bacterial growth and extracellular polysaccharide synthesis of cariogenic plaque bacteria as shown in the above examples. Therefore, the salt form of medium-chain fatty acids in this invention can be largely used as prophylactic and therapeutics of dental caries and periodontal disease due to the noticeable inhibition of dental caries.

Particularly, the salt form of lauric acid almost completely inhibits the acid production ability and the bacterial growth of major acidogenic plaque bacteria among cariogenic plaque bacteria. This is true not only at high concentration and neutral pH but also at low concentration (1 mM) and acidic pH, so this can be used as a strong inhibitor of dental caries.

Pharmaceutical composition of the present invention may contain lectins and/or fluoride compound in addition to medium-chain fatty acids, and the effect can be further improved in this case.

Dental caries inhibitor of this invention has a remarkable function of inhibiting dental caries and has no side effects and contraindication. Thus everybody can use it and it can be supplied at low prices. And products of various formations can be developed.

What is claimed is:

1. Pharmaceutical composition for prevention and treatment of dental caries consisting essentially of medium-chain fatty acids and lectins, as an effective component.

2. Pharmaceutical composition for prevention and treatment of dental caries according to claim 1, further comprising fluoride compounds as effective component.

3. Pharmaceutical composition for prevention and treatment of dental caries according to claim 1, wherein the medium-chain fatty acids are selected from the group of lauric acid, capric acid, nonanoic acid, the salts thereof and mixtures thereof.

4. Pharmaceutical composition for prevention and treatment of dental caries according to claim 1, wherein the composition is in the form of a solution.

5. Pharmaceutical composition for prevention and treatment of dental caries according to claim 1, wherein the composition is in the form of a toothpaste.

6. Pharmaceutical composition for prevention and treatment of dental caries according to claim 1, wherein the composition is in the form of a gum.

7. Pharmaceutical composition for prevention and treatment of dental caries according to claim 1, wherein the composition is in the form of a spray.

\* \* \* \* \*